United States Patent [19]

McMorrow et al.

[11] 4,302,956

[45] Dec. 1, 1981

[54] BLOOD IDENTIFICATION MEANS

[76] Inventors: John J. McMorrow, 55 Florence Ave., Oyster Bay, N.Y. 11771; Harold Kaplan, 37 Oakland Beach Ave., Rye, N.Y. 10580; Frederick Sommerhalter, Jr., 98 Kellog St., Oyster Bay, N.Y. 11771

[21] Appl. No.: 60,641

[22] Filed: Jul. 25, 1979

[51] Int. Cl.³ .............................................. E05B 37/02
[52] U.S. Cl. ........................................ 70/312; 70/23; 70/318
[58] Field of Search ...................... 70/23, 64, 65, 312, 70/316, 317, 318; 128/214 D

[56] References Cited

U.S. PATENT DOCUMENTS 1,591,777  7/1926  Putman ................................. 70/312
2,189,342  2/1940  Eber .................................... 70/318

FOREIGN PATENT DOCUMENTS 492031  2/1919  France .................................. 70/65

Primary Examiner—Robert L. Wolfe
Attorney, Agent, or Firm—James P. Malone

[57] ABSTRACT

Coded lock for blood transfusion bags of the type having a locking flap. A pin extends through the locking flap of the bag. A numerically coded lock locks the pin through the flaps. A numerical code is set into the lock. The numerical code is attached to the patient's wrist. At the patient's location the nurse reads the code attached to the patient's wrist and opens the bag.

1 Claim, 7 Drawing Figures

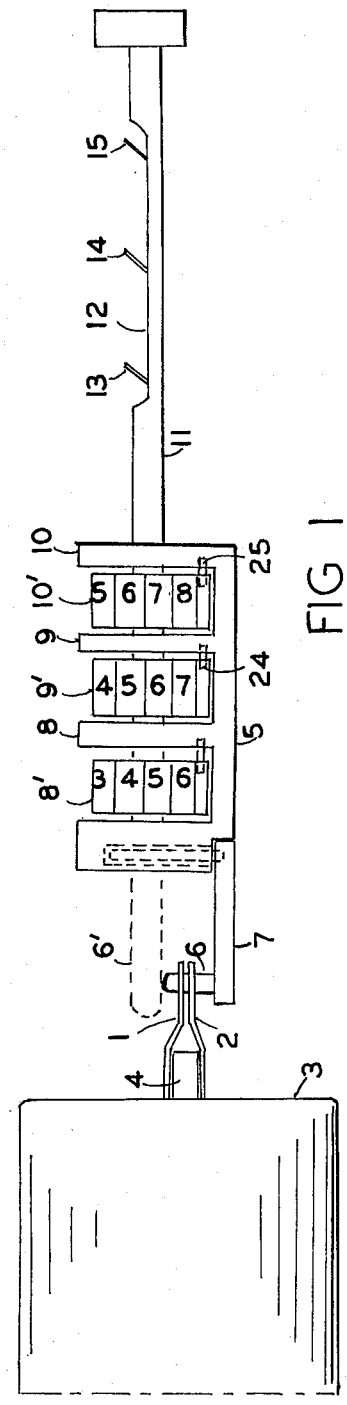
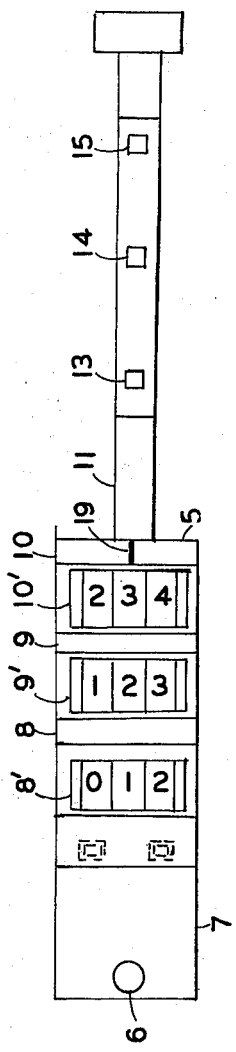
FIG 2
FIG 1
JOHN DOE 123
FIG 3

BLOOD IDENTIFICATION MEANS

This invention relates to blood identification means and more particular to means for minimizing the possibility of error when administering blood to a patient.

In virtually all hospitals, there is a Blood Bank Department which provides blood for infusion into the patients as needed. It is very important that this blood be of the proper blood type since the administration of the wrong blood type can lead to serious and possible fatal consequences.

In order to insure that the patients get the proper type blood, the patient's own blood is typed by testing, and the proper type blood is sent out from the Blood Bank to be administered to the patient. Due to the fact that the blood transfusion bag passes through a number of hands, a bag could be and sometimes is delivered and administered to the wrong patient, or the wrong type delivered.

The present invention tends to eliminate any possibility of error. The present invention provides a coded lock adapted to lock the blood bag at the Blood Bank. The lock being coded for a particular patient. The patient has a coded number on his wrist band which is attached to all patients according to standard hospital procedure. The nurse or other person who is going to administer the blood first looks at the number on the patient's wrist and then sets that number into the combination lock in order to gain access to the blood. Therefore, once the bag of blood plasma leaves the Blood Bank there is little or no possibility of error in delivery of the proper type blood to the proper patient.

This Application is an improvement of Application Ser. No. 941,657, filed Sept. 11, 1978 and now U.S. Pat. No. 4,205,101 of the same title.

Accordingly, a principal object of the invention is to provide new and improved identification means for delivery of blood to a patient.

Another object of the invention is to provide new and improved blood identification means comprising a coded lock locking the blood bag, the lock being coded for a particular patient, and means attached to the patient providing the code for the lock.

Another object of the invention is to provide new and improved blood identification means wherein a blood bag has a combination lock which is opened by using the code from the patient's wrist band.

Another object of the invention is to provide new and improved means for coded locking of blood bags of the type having a locking flap, comprising, a pin adapted to extend through the locking flap, a numerically coded lock adapted to lock said pin through said flaps and means to set a numerical code into said lock.

These and other objects of the invention will be apparent from the following specification and drawings of which:

FIG. 1 shows a side view of an embodiment of the invention.

FIG. 2 shows a top view of FIG. 1.

FIG. 3 shows a typical patient's wrist band with identifying number.

Figure 4:
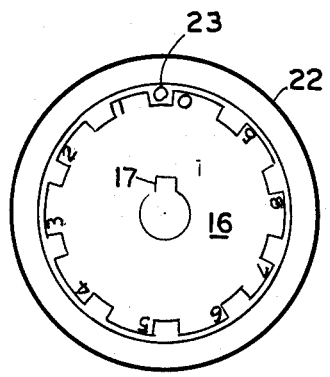
FIG. 4 is a front view of the inner disc.

Referring to FIGS. 1 and 2, the invention comprises a combination lock which is adapted to lock the locking flap or flaps, 1 and 2 on the blood bag 3, so that the flaps cover the spout 4 of the blood bag. The blood is fed from the bag in conventional manner by inserting a needle type device through spout 4 and hanging the bag up with the spout down.

The combination lock of the present invention comprises a casing 5. Removably mounted in the casing is a bag locking pin 6. The pin is mounted in a holder 7 which slides into a slot in the casing 1. With this arrangement, different type bag locking pin assemblies can be used for locking bags of different configurations.

The lock assembly comprises the casing 5 which has partitions 8, 9 and 10 and index mark 19. Between the partitions are rotatably mounted a plurality of numbered disc assemblies 8', 9', and 10'. The disc assemblies and the casing have a central shaftway and the disc assemblies have a large notch in the central shaftway. A plunger 11, is adapted to be inserted through the central shaftways into a locking relationship to the bag locking pin 6 as shown by the dotted lines 6'. The plunger 11 has a recess 12, in which is mounted a plurality of flexible retaining members 13, 14 and 15, so that the plunger can be pushed into locking position regardless of the setting of the discs. However, the plunger cannot be pulled out to unlock the bag unless the discs have been set to the proper code with the center notches aligned, as will be explained.

FIG. 3 shows a typical patient's wrist band having the patient's number, being "1 2 3".

Figure 5:
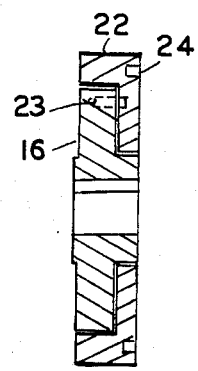
FIG. 5 is a sectional view of the inner and outer discs.
Figure 6:
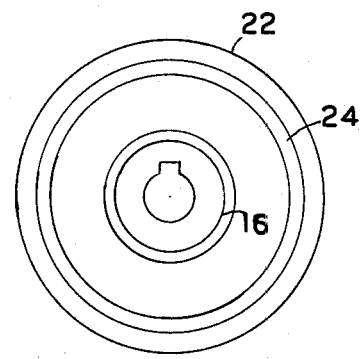
FIG. 6 is a rear view of the outer disc.

FIGS. 4, 5 and 6, show the disc assemblies. Each disc assembly comprises an inner disc 16 having a center shaftway with a large notch 17. The notch is sized to allow the retaining members 13, 14 and 15 to pass through when the discs are properly lined up in the predetermined code relationship. The plunger 11 has a fixed angular relationship in the casing 5 so that the retaining members 13, 14, and 15, will always be in top position with respect to the casing.

Figure 7:
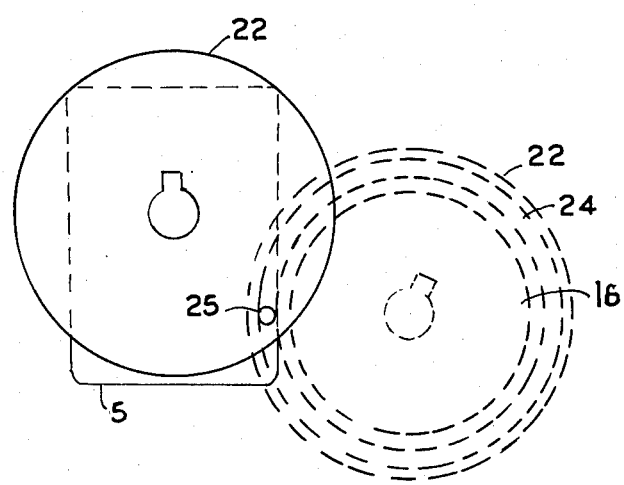
FIG. 7 is a side view illustrating the coding position of the inner and outer discs.

The inner disc also has ten numbered notches around its periphery. The inner disc 16 fits inside the outer disc 22. The outer disc has an indexing pin 23 which is adapted to fit in one of the notches 20, 21, etc., for the purpose of indexing the inner and outer disc members together. On the rear of the outer disc member is a circular slot 24 which receives retaining pins 25 which are mounted in the partitions of the casing. The purpose of this pin and slot arrangement is to retain the disc assemblies inside the casing but to permit partial rotation of the disc assembly to the side of the casing as shown in FIG. 7 for the purpose of indexing the inner and outer discs together. The notches in the inner disc are numbered in counter-clockwise direction. The numbers on the outer surface of the outer disc increase in clockwise direction.

The casing 5 has an indexing mark 19 for the purpose of setting the disc assemblies in accordance with the code. As shown in FIG. 2, the disc assemblies are set to the number "1 2 3". When the blood bag is delivered to the patient, the nurse reads the patient's number "1 2 3" off his or her wrist band and then sets the disc assemblies to member "1 2 3" as shown in FIG. 2.

The code number is set into the lock as follows:

The first disc assembly is rotated out to the side as shown in FIG. 7.

The inner disc 16 is then moved slightly away from the outer disc and out of engagement with the pin 23 so that the inner disc can be rotated with respect to the outer disc. Assuming we wish to set the number "1" on this disc assembly, the inner disc is rotated so that the number "1" is to the left of the pin 23 which then extends through the notch number "1". The inner and outer discs are then snapped together and rotated back into the casing. This disc assembly is now set so that when the number "1" on the outer surface of the outer disc 22 is rotated to the top and aligned with the indexing mark 19 on the casing 5, the large center notch will extend straight up. The partitions in the casing are spaced so as to hold the inner and outer disc in indexed relation.

The outer two disc assemblies are indexed in similar manner to the numbers "2 and 3" so that the code "1 2 3" is set into the lock.

The lock is then attached to the bag at the Blood Bank by inserting the pin 6 through the holes in the flaps 1 and 2 of the blood bag. The plunger 11 is then pushed in so that it comes into locking relation with the top of the pin 6 as shown by the dotted lines 6'. The disc assemblies are then rotated randomly to lock the plunger.

The locked bag is then transported to the patient's location. The patient's nurse then reads the code number off the patient's wrist band and sets the code on the outer discs. This lines up the notches in the disc assemblies so that the plunger can be retracted and unlock the bag. Note, that all three disc assemblies have to be set in a proper code in order to permit any retraction movement of the plunger. If any one of the disc assemblies is not set correctly the plunger will not retract at all since one or all of the other retaining members 13, 14 and 15, will be in contact with the un-notched portion of one or more inner discs.

Therefore, once the bag of blood plasma leaves the blood bank there is little or no possibility of error in delivery of the proper type blood to the proper patient.

The combination lock of the present invention may be made inexpensively of molded plastic parts. The lock of the present invention is not specifically limited for use with blood bags but may have other applications. For instance, it could lock chains together, for instance, to secure bicycles.

The disc assemblies preferably have different colors to minimize errors. The patient's wrist band may also have corresponding colors on the different numbers.

The bag locking pin assembly has a bayonet type connection which fits into the case. This connection preferably has two prongs which fit into a corresponding slot in the case which bends the prongs over the plunger when the plunger is in locked position. Therefore, the plunger locks the pin assembly to the case.

Please note that the blood bag is not labeled with the patient's number in the Blood Bank. A blood specimen from the patient is compared with that in the bag for compatability, if compatable, the bag is then locked with the lock having the patient's number set into the lock.

Therefore there are no labels or other paper work which can cause errors. The only way that the number to open the bag can be obtained is from the patient's wrist so that errors in delivery of the proper bag to the proper blood type to the proper patient are completely eliminated.

It is claimed:
1. Means for coded locking of blood bags of the type having a locking part, comprising:
   a pin adapted to extend through the locking flap,
   a numerically coded lock adapted to lock said pin through said flaps and
   means to set a numerical code into said lock,
   the lock comprising,
   a casing,
   a plurality of numbered disc means rotatably mounted in the casing, the disc means having a central notched shaftway,
   a plunger adapted to extend through said casing and said disc means into locking relation to said pin,
   a plurality of retarding elements mounted on said plunger whereby the plunger can be withdrawn only if the correct code is set on the numbered disc means,
   the number disc means comprising,
   an outer numbered disc,
   an inner disc numbered and notched around its periphery, the inner disc having a central shaftway with a notch sized to pass the retarding members on said plunger, and
   an outer disc having an indexing pin so that the inner and outer discs may be indexed together,
   the casing having a plurality of partitions to receive the inner and outer discs in indexed position,
   wherein the partitions each having a retaining pin and the outer disc has a circular retainer slot to engage the retaining pin so that the inner and outer discs might be rotated out of the casing for the purpose of indexing the inner and outer discs with respect to each other.

* * * * *